United States Patent [19]

Brunkan

[11] Patent Number: 4,877,027
[45] Date of Patent: Oct. 31, 1989

[54] HEARING SYSTEM

[76] Inventor: Wayne B. Brunkan, P.O. Box 2411, Goleta, Calif. 93118

[21] Appl. No.: 202,679

[22] Filed: Jun. 6, 1988

[51] Int. Cl.$^4$ .............................................. A61N 5/00
[52] U.S. Cl. ................................................ 128/420.5
[58] Field of Search ................ 128/420.5, 804, 419 R, 128/421, 422, 746; 381/68

[56] References Cited

U.S. PATENT DOCUMENTS 3,629,521 12/1971 Puharich et al. ................. 128/402.5
3,766,331 10/1973 Zink ................................ 128/420.5

OTHER PUBLICATIONS

Cain et al, "Mammalian Auditory Responses . . .", IEEE Trans Biomed Eng, pp. 288–293, 1978.
Frey et al, "Human Perception . . . Energy" Science, 181,356–358, 1973.
Jaski, "Radio Waves & Life", Radio-Electronics, pp. 45–45, Sep. 1960.
*Microwave Auditory Effects and Applications*, Lin, 1978, pp. 176–177.

Primary Examiner—Lee S. Cohen
Attorney, Agent, or Firm—Harry W. Brelsford

[57] ABSTRACT

Sound is induced in the head of a person by radiating the head with microwaves in the range of 100 megahertz to 10,000 megahertz that are modulated with a particular waveform. The waveform consists of frequency modulated bursts. Each burst is made up of ten to twenty uniformly spaced pulses grouped tightly together. The burst width is between 500 nanoseconds and 100 microseconds. The pulse width is in the range of 10 nanoseconds to 1 microsecond. The bursts are frequency modulated by the audio input to create the sensation of hearing in the person whose head is irradiated.

8 Claims, 1 Drawing Sheet

BURST → | ← RANGE 500 NANO SEC. TO 100 MICRO SEC.    PULSE → | ← 10 NANO SEC. TO 1 MICRO SEC.

HEARING SYSTEM

This invention relates to a hearing system for human beings in which high frequency electromagnetic energy is projected through the air to the head of a human being and the electromagnetic energy is modulated to create signals that can be discerned by the human being regardless of the hearing ability of the person.

THE PRIOR ART

Various types of apparatus and modes of application have been proposed and tried to inject intelligible sounds into the heads of human beings. Some of these have been devised to simulate speech and other sounds in deaf persons and other systems have been used to inject intelligible signals in persons of good hearing, but bypassing the normal human hearing organs.

U.S. Pat. No. 3,629,521 issued Dec. 21, 1971 describes the use of a pair of electrodes applied to a person's head to inject speech into the head of a deaf person. An oscillator creates a carrier in the range of 18 to 36 KHz that is amplitude modulated by a microphone.

Science magazine volume 181, page 356 describes a hearing system utilizing a radio frequency carrier of 1.245 GHz delivered through the air by means of a waveguide and horn antenna. The carrier was pulsed at the rate of 50 pulses per second. The human test subject reported a buzzing sound and the intensity varied with the peak power.

Similar methods of creating "clicks" inside the human head are reported in I.E.E.E. Transactions of Biomedical Engineering, volume BME 25, No. 3, May 1978.

The transmission of intelligible speech by audio modulated Microwave is described in the book Microwave Auditory Effects and Applications by James C. Lin 1978 publisher Charles C. Thomas.

BRIEF SUMMARY OF THE INVENTION

I have discovered that a pulsed signal on a radio frequency carrier of about 1,000 megahertz (1000 MHz) is effective in creating intelligible signals inside the head of a person if this electromagnetic (EM) energy is projected through the air to the head of the person. Intelligible signals are applied to the carrier by microphone or other audio source and I cause the bursts to be frequency modulated. The bursts are composed of a group of pulses. The pulses are carefully selected for peak strength and pulse width. Various objects, advantages and features of the invention will be apparent in the specification and claims.

BRIEF DESCRIPTION OF THE DRAWINGS

In the drawings forming an integral part of this specification.

DETAILED DESCRIPTION OF THE INVENTION

Inasmuch as microwaves can damage human tissue, any projected energy must be carefully regulated to stay within safe limits. The guideline for 1,000 MHz, set by the American Standards Institute, is 3.3 mw/cm2 (3.3 milliwatts per square centimeter). The apparatus described herein must be regulated to stay within this upper limit.

Figure 1:
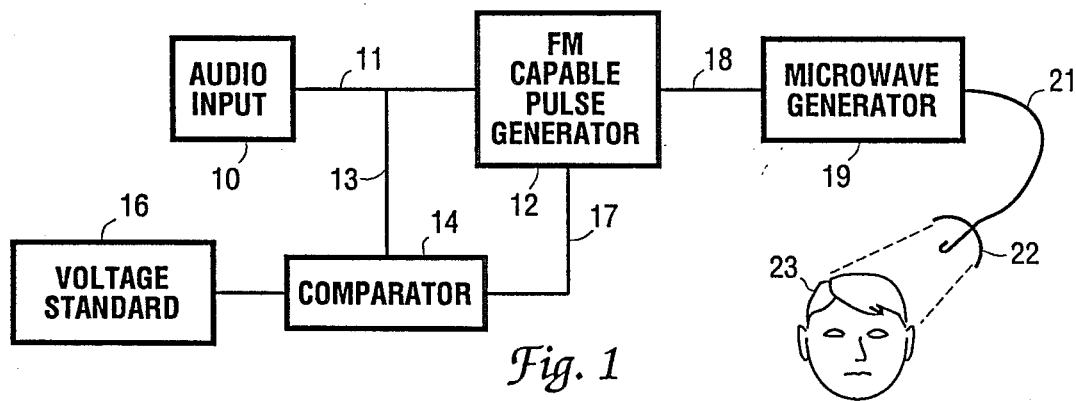
FIG. 1 is a block diagram of the system of the invention.

Referring to FIG. 1 a microphone 10 or other generator of audio frequencies, delivers its output by wire 11 to an FM capable pulse generator 12 and by branch wire 13 to a comparator 14. The comparator 14 also receives a signal from a voltage standard 16. When the peak voltage of the audio generator 10 falls below the standard 16 the comparator delivers a signal by wire 17 to the FM capable pulse generator 12 to shut down the pulse generator 12. This avoids spurious signals being generated. The output of the FM pulse generator 12 is delivered by wire 18 to a microwave generator 19 which delivers its output to the head of a human being 23. In this fashion the person 23 is radiated with microwaves that are in short bursts.

The microwave generator 19 operates at a steady frequency presently preferred at 1,000 megahertz (1,000 million). I presently prefer to pulse the microwave energy at pulse widths of 10 nanoseconds to 1 microsecond. For any one setting of the FM capable generator 12, this width is fixed. The pulses are arranged in bursts. The timing between bursts is controlled by the height of the audio envelope above the voltage standard line. In addition the bursts are spaced from one another at a non-uniform rate of 1 to 100 KHz. This non-uniform spacing of bursts is created in the FM capable generator 12.

Figure 2:
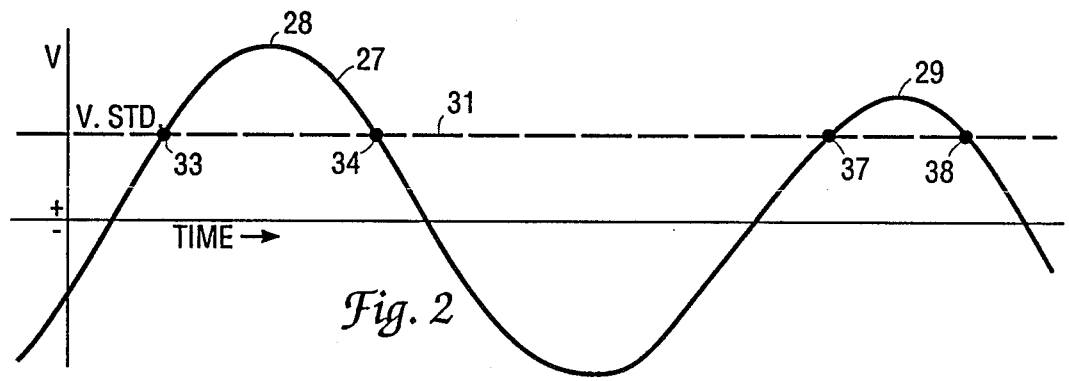
FIG. 2 is a diagram of an audio wave which is the input to be perceived by the recipient.

Referring to FIG. 2 there is illustrated an audio wave 27 generated by the audio input 10 wherein the horizontal axis is time and the vertical axis is voltage. For illustrative purposes the wave 27 is shown as having a voltage peak 28 on the left part of FIG. 2 and a voltage peak 29 of the right side of FIG. 2. The voltage standard 16 of FIG. 1 generates a dc voltage designated at 31 in FIG. 2. This standard voltage is preferably at about 50% of the peak voltage 28. The comparator 14 of FIG. 1 actuates the FM capable generator 12 only when the positive envelope of the audio wave 27 exceeds the voltage standard. The negative portions of the audio wave are not utilized.

Figure 3:
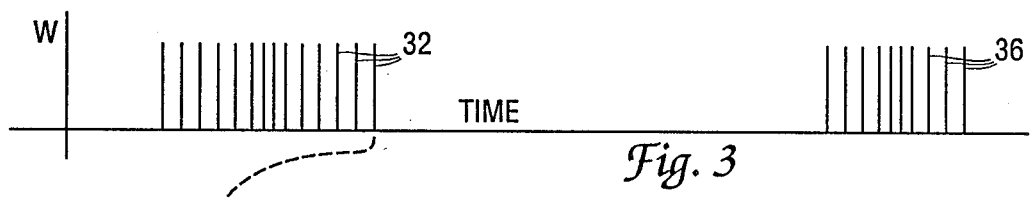
FIG. 3 is a diagram on the same time coordinate as FIG. 2 showing bursts that are frequency modulated by the wave form of FIG. 2.

Referring now to FIG. 3 there is illustrated two groups of bursts of microwave energy that are delivered by the antenna 22 of FIG. 1 to the head of the person 23. FIG. 3 has a horizontal time axis identical to the time axis of FIG. 2 and has a vertical axis that in this case represents the power of the microwaves from generator 19. At the left part of FIG. 3 are a plurality of microwave bursts 32 that occur on the time axis from the point of intersection of the standard voltage 31 with the positive part of the audio wave 27, designated as the time point 33 to time point 34 on FIG. 2. It will be noted in FIG. 3 that the bursts 32 are non-uniform in spacing and that they are closer together at the time of maximum audio voltage 28 and are more spread out toward the time points 33 and 34. This is the frequency modulation effected by the FM pulse generator 12.

Referring to the right part of FIG. 3 there are a plurality of microwave bursts 36 that are fewer in number and over a shorter time period than the pulses 32. These extend on the time axis of FIG. 2 from point 37 to point 38. These bursts 36 are also frequency modulated with the closest groupings appearing opposite peak 29 of FIG. 2 and greater spacing near time points 37 and 38.

Figures 4, 5:
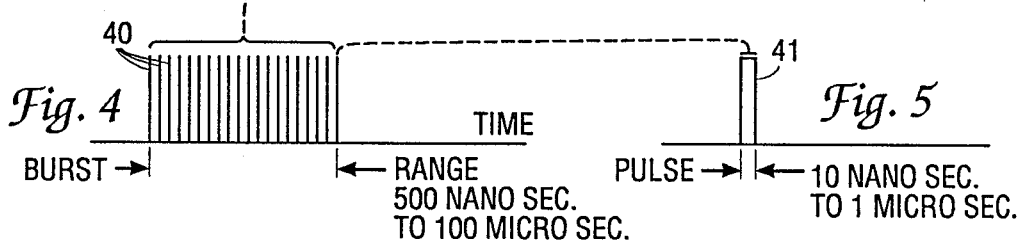
FIG. 4 shows, on an enlarged time coordinate, that each vertical line depicted in FIG. 3 is a burst of pulses. (A burst is a group of pulses).
FIG. 5 shows, on a further enlarged time coordinate, a single continues pulse, Depicted as'a vertical line in FIG. 4.

Referring now to FIG. 4 there is illustrated the fact that a single burst shown as straight lines 32 or 36 on FIG. 3 are made up of ten to twenty separate microwave pulses. The duration of the burst is between 500 nanoseconds and 100 microseconds, with an optimum of 2 microseconds. The duration of each pulse within the burst is 10 nanoseconds to 1 microsecond and a time duration of 100 nanoseconds is preferred. The bursts 32 of FIG. 3 are spaced non-uniformly from each other caused by the frequency modulation of 12. FIG. 4 depicts a burst. Each vertical line 40 in FIG. 4 represents a single pulse. Each pulse is represented by the envelope 41 of FIG. 5. The pulses within a burst are spaced uniformly from eachother. The spacing between pulses may vary from 5 nanoseconds to 10 microseconds.

Referring now to FIG. 3, the concentration of bursts 32 opposite the peak 28 of FIG. 2 can be expressed as a frequency of repetition. I presently prefer to adjust the FM capable generator 12 to have a maximum frequency of repetition in the range of 25 Khz to 100 Khz. I deliberately keep this range low to reduce the amount of heating caused by the microwaves. The wider spacing of the pulses 32 opposite the cutoff points 33 and 34 of FIG. 2 can also be expressed as a frequency of reptition and I presently prefer a minimum repetition rate of 1 KHz. I find that this low repetition rate, altnough in the audio range, does not disrupt the transmission of auoio intelligence to the person 23. The aim, again, is to reduce the amount of heat transmitted to the subject 23.

OPERATION

Referring to FIG. 1, the intelligence to be perceived by the person 23 is introduced at the audio source 10 which may be a microphone for voice, or a tape player for music, instruction, etc. This audio signal is transmitted to the FM capable generator 12 and to the comparator 14. The comparator 14 compares the positive portions of the audio wave with voltage from the voltage standard 16 and when the audio wave instantaneously exceeds the standard voltage, the FM generator is actuated by the wire 17 connecting the comparator 14 and the FM generator 12. The FM generator 12 then sends a plurality of signals to the microwave generator 19 at each peak of the audio wave above the voltage standard.

This is shown graphically in FIGS. 2–5. The audio signal 27 of FIG. 2 exceeds the standard voltage 31 at point 33 whereupon the FM generator 12 starts emitting burst signals 32 at its lowest frequency of about 1 Khz. As time progresses past point 33 the voltage above the standard increases and the FM generator 12 responds by making the burst signals closer together until at peak 28 the maximum density of burst signals 32 is achieved, for example at a frequency of 50 Khz. The time duration of each pulse 40 (FIG. 4) is also controlled by a fixed adjustment of the FM generator 12 and for example the duration may be 100 nanoseconds.

The frequency modulated burst signals are delivered by FM generator 12 to the microwave generator as interrupted dc and the microwave generator is turned on in response to each pulse 40 and its output is delivered by coaxial cable 21 to the parabolic antenna 22 to project microwaves onto the head of a person 23. These microwaves penetrate the brain enough so that the electrical activity inside of the brain produces the sensation of sound. When the parameters are adjusted for the particular individual, he perceives intelligible audio, entirely independently of his external hearlng organs.

PRESENTLY PREFERRED QUANTITIES

As mentioned previously, I prefer rhat the standard voltage 31 of FIG. 2 be about 50% of peak audio voltage. This not only helps to reduce heating in the person 2 but also reduces spurious audio. This 50% is not vital and the useful range is 25% to 85% of peak audio.

The minimum burst repetition frequency (for example at time points 33 and 34) is preferably 1 KHz and the maximum repetition frequency is in the range of 25 KHz to 100 KHz, with the lower frequencies resulting in less heating.

The time duration of each individual pulse of microwave radiation is in the range of 10 nanoseconds to 1 microsecond as indicated in FIG. 5, with the shorter time periods resulting in less heating.

CONTROL OF POWER OUTPUT

As stated above, I maintain the power output of the parabolic antenna 22 within the present safe standard of 3.3 mw/cm2 (3.3 milliwatts per square centimeter). I control the power output by controlling the strengtn of the audio modulation. This results in a duty cycle of 0.005, the decimal measure of the time in any second that the transmitter is on full power. The peak power level can be between 500 mw and 5 w and at 0.005 duty cycle these peaks will result in an average power of 2.5 mw and 25 mw respectively. However, these values are further reduced by adjusting the audio modulation so that zero input produces a zero output. Since a voice signal, for example, is at maximum amplitude only a small fraction of the rime, the average power will be below the 3.3 mw/cm2 standard, even with 5 watts peak power.

THEORY OF OPERATION

I have not been able to experiment to determine how my microwave system works, but from my interpretation of prior work done in this field I believe that the process is as follows. Any group of bursts related to the audio ek 28 of FIG. 2 causes an increasing ultrasonic build up within the head of a human being starting with a low level for the first bursts pulses and building up to a high level with the last bursts pulses of a group. This buildup, I believe, causes the direct discharge of random brain neurons. These discharges at audio frequency create a perception of sound. This process, I believe, bypasses the normal hearing organs and can create sound in a person who is nerve-dead deaf. However, this theory of operation is only my guess and may prove to be in error in the future.

APPARATUS

The apparatus of FIG. 1 for carrying out my invention may include as a microwave generator Model PH40K of Applied Microwave Laboratories and described as Signal Source. The cable 21 connecting the microwave generator 19 and the antenna is RG8 coaxial cable by Belden Industries. The antenna 22 may be a standard parabolic antenna. The FM generator 12 has to be specially built to include the spacing runction which is obtained by a frequency generator built into a srandard FM generator.

I have described my invention witn respect to a presently preferred embodiment as required by the patent statutes. It will be apparent to those skilled in the technology that many variations, modification and additions can be made. All such variations, modifications and additions that come within the true spirit and scope of the invention are included in the claims.

I claim:

1. Apparatus for creating human hearing comprising:
   (a) an audio source for creating electrical audio waves having positive peaks;
   (b) a frequency modulator generator connected to the audio source to create frequency modulated bursts;
   (c) a source of constant voltage to create a voltage standard that is in the range of 25% to 85% of the peak voltage of the audio waves;
   (d) a comparator connected to the voltage source and the audio source to compare the instantaneous voltage of the waves from the audio source with the voltage standard;
   (e) a connection of the comparator to the frequency modulator generator to activate the frequency modulator generator when the instantaneous voltage of the audio wave exceeds the standard voltage;
   (f) a microwave generator creating microwaves in the range of 100 megahertz to 10,000 megahertz and connected to the frequency modulator generator, generating microwaves only when pulsed by the frequency modulator generator; and
   (g) an antenna connected to the microwave generator to radiate the head of a human being to produce the sounds of the audio source.

2. Apparatus as set forth in claim 1 wherein the frequency generating range of the frequency modulator generator is 1 Khz to 100 KHz for bursts and 100 KHz to 20 MHZ for pulses within a burst.

3. Apparatus as set forth in claim 1 wherein the frequency generating range of the frequency modulator generator is one Khz to 100 KHz for bursts and 100 KHz to 20 MHZ for pulses within a burst and the duration of each pulse of the frequency modulator generator is in the range of 10 nanoseconds to 1 microsecond.

4. Apparatus as set forth in claim 1 wherein the voltage standard is approximately 50% of the peak of the audio waves.

5. Apparatus as set forth in claim 1 wherein the antenna is of the type that projects the microwaves in space to the head of a person.

6. Apparatus for creating human hearing comprising:
   (a) an oscillator creating an electromagnetic carrier wave at a selected frequency in the range of 100 Mhz to 10,000 Mhz;
   (b) a pulse generator connected to said oscillator to pulse the carrier with pulses having a width in the range of 10 nanoseconds to 1 microsecond with a minimum spacing between pulses of about 25 nanoseconds;
   (c) a frequency modulator connected to the pulse generator;
   (d) an audio signal generator connected to the modulator which modulates the pulses in accordance with the audio signal; and
   (e) a transmitting antenna connected to the oscillator to transmit the carrier wave as thus modified to project the electromagnetic energy through space to the head of a person.

7. Apparatus as set forth in claim 6 wherein the modulator is a frequency modulator to vary the density of bursts within an audio envelope as a function of the audio amplitude.

8. The method of irradiating a person's head to produce sound in the head of the person comprising
   (a) irridiating the head of a person with microwaves in the range of 100 Mhz to 10,000 Mhz;
   (b) pulsing said microwaves with pulses in the range of 10 nanoseconds to 1 microsecond; and
   (c) frequency modulating groups of pulses called bursts by audio waves wherein the modulation extends from 1 Khz to 100 Khz.

* * * * *